US011230977B2

(12) United States Patent
Vierling et al.

(10) Patent No.: US 11,230,977 B2
(45) Date of Patent: Jan. 25, 2022

(54) METHOD OF OPTIMIZING THE LIMITATION OF DUST EMISSIONS FOR GAS TURBINES FUELED WITH HEAVY FUEL OIL

(71) Applicant: GE ENERGY PRODUCTS FRANCE SNC, Belfort (FR)

(72) Inventors: Matthieu Vierling, Dampierre-les-Bois (FR); Pierre Montagne, Belfort (FR); Sven Catrin, Offemont (FR); Ezio Pena Saavedra, Cravanche (FR); Mohamad-Maher Aboujaib, Evette Salbert (FR)

(73) Assignee: General Electric Company, Schenectady, NY (US)

( * ) Notice: Subject to any disclaimer, the term of this patent is extended or adjusted under 35 U.S.C. 154(b) by 304 days.

(21) Appl. No.: 16/227,384

(22) Filed: Dec. 20, 2018

(65) Prior Publication Data

US 2019/0195142 A1 Jun. 27, 2019

(51) Int. Cl.
*F02C 9/00* (2006.01)
*F02C 3/30* (2006.01)
(Continued)

(52) U.S. Cl.
CPC .............. *F02C 9/00* (2013.01); *F01D 17/085* (2013.01); *F02C 3/24* (2013.01); *F02C 3/30* (2013.01); *F02C 7/08* (2013.01); *F02C 7/224* (2013.01); *F23D 11/44* (2013.01); *F23K 5/10* (2013.01); *F02C 6/08* (2013.01); *F02C 9/18* (2013.01);
(Continued)

(58) Field of Classification Search
CPC ..... F23R 3/40; F23K 5/08; F23K 5/10; F23K 2300/00; F23K 2301/10; F23K 2301/103; F23N 5/003; F02C 3/20; F02C 3/24; F02C 9/00; F02C 9/18; F02C 7/24; F02C 7/224; F02C 3/30
See application file for complete search history.

(56) References Cited

U.S. PATENT DOCUMENTS

2007/0220873 A1\* 9/2007 Bosteels ................... F01N 3/10
60/299
2010/0186387 A1\* 7/2010 Perry ..................... C10L 1/2633
60/287
(Continued)

FOREIGN PATENT DOCUMENTS

EP 3150825 A1 4/2017
FR 1559155 A1 9/2015

*Primary Examiner* — Craig Kim
(74) *Attorney, Agent, or Firm* — Dority & Manning, P.A.

(57) ABSTRACT

Method for optimizing the limitation of dust emissions from a gas turbine or combustion plant comprising a line for supplying liquid fuel oil, a line for generating fuel oil atomizing air, and a central controller, wherein: a first definition step, starting from a nominal temperature of the fuel oil and a nominal pressure ratio of the atomizing air of the fuel oil, and by controlling the injection of the soot inhibitor, of a nominal operating point corresponding to the maximum permissible level of emitted dust; a second step of controlling a first parameter, taken from the group of the fuel oil temperature and the pressure ratio of the fuel oil atomizing air, in order to reach another operating point; and a third step of controlling the soot inhibitor injection to achieve the maximum permissible level of emitted dust.

13 Claims, 3 Drawing Sheets

(51) Int. Cl.
*F23K 5/10* (2006.01)
*F01D 17/08* (2006.01)
*F02C 3/24* (2006.01)
*F02C 7/08* (2006.01)
*F02C 7/224* (2006.01)
*F23D 11/44* (2006.01)
*F02C 9/20* (2006.01)
*F02M 19/03* (2006.01)
*F23D 11/10* (2006.01)
*F02C 6/08* (2006.01)
*F02C 9/18* (2006.01)
*G01N 33/00* (2006.01)

(52) U.S. Cl.
CPC ............... *F02C 9/20* (2013.01); *F02M 19/03* (2013.01); *F05D 2270/081* (2013.01); *F05D 2270/0831* (2013.01); *F23D 11/10* (2013.01); *F23K 2300/103* (2020.05); *F23N 2237/14* (2020.01); *F23N 2239/06* (2020.01); *G01N 33/0004* (2013.01)

(56) References Cited

U.S. PATENT DOCUMENTS

2017/0115007 A1* 4/2017 Aboujaib ............... F02C 3/30
2017/0292446 A1* 10/2017 Hwang ............... B01J 19/2485

\* cited by examiner

— FIG. 1 —

METHOD OF OPTIMIZING THE LIMITATION OF DUST EMISSIONS FOR GAS TURBINES FUELED WITH HEAVY FUEL OIL

FIELD OF THE INVENTION

The invention relates to a method of optimizing the limitation of dust emissions for gas turbines or combustion plants fueled with heavy fuel oil.

BACKGROUND OF THE DISCLOSURE

A wide range of liquid fuels is available for the supply of combustion turbines. These include heavy fuel oils, crude oils, heavy or light distillates, gas oils, kerosene, and naphtha.

In ambient temperature conditions, heavy fuel oils generally have a high viscosity that does not permit them to be transported in pipes. In practice, a heating device is used to increase the temperature of the heavy fuel oil to a previously defined temperature level (nominal temperature) that has the effect of significantly reducing the viscosity of said heavy fuel oil for use in a combustion system. There are different types of heating devices, based on heat exchangers, operating for example with hot water, steam or electrical resistance. The heating device can increase, maintain or reduce the temperature of said heavy fuel oil depending on the objective of the operator of a gas turbine or combustion plant. Generally, a heating device can change the temperature of the heavy fuel oil in just minutes.

Any conventional fuel system fueled by heavy fuel oil generates dust or solid particles that are transported by the flue gas stream. Depending on the performance of the combustion system, heavy fuel oils can generate more or less solid particles that are released to the atmosphere at the chimney outlet.

Among the solid particles, carbonaceous soot corresponds to the organic fraction of the dusts, and comprises mainly carbon, hydrogen and optionally oxygen and nitrogen, and may also contain a mineral fraction (ash) generally consisting of alkaline metals or heavy metals. In addition, soot and ash can agglomerate and form layers of solid deposits on the surface of the gas turbine components traversed by the combustion gases; this phenomenon can be observed up to the chimney.

The generation of soot is favored by various factors, in particular:
  A poor atomization efficiency of the heavy fuel oil can generate particles of unburned compounds (incomplete combustion of larger fuel droplets). The atomization efficiency depends on the temperature of the heavy fuel oil and its viscosity, as well as the pressure of the air used for this operation.
  The water content of the fuel can cause a cooling effect of the flame that generates fumes (lack of heat energy in the combustion system).

Worldwide, gas turbines are subject to air emissions regulations that set the maximum limit values for the concentration of dust released into the atmosphere. These concentration levels are variable depending on the country and the environment specific to each gas turbine. For example, in the context of the use of a heavy fuel oil, when a combustion turbine operates in nominal mode, the maximum value of dust discharge to the atmosphere for a stationary combustion turbine located in a little industrialized environment is 50 mg/Nm$^3$ (2008 World Bank Emission Guidelines).

In order to limit the quantity of solid particles emitted, a soot inhibitor, an organic and metallic-based additive generally introduced into the liquid fuel is generally used. There are different types of soot inhibitors that can reduce emissions in installations, such as fat-soluble additives based on cerium. The choice of soot inhibitor depends on the type of fuel, the type of installation used and the maximum concentration of solid particles imposed by local/global regulations.

Methods for inhibiting soot emissions exist, for example as described in document FR1559155.

Experience shows that injection of the soot inhibitor has an almost instantaneous reduction effect on particle emissions. In addition, under certain conditions, the effect of the inhibitor can have a certain inertia due to its deposition on equipment downstream of the combustion, such as combined-cycle boilers, through which the combustion gases pass. Thus, even if the inhibitor flow rate is interrupted or decreased, the effect of the inhibitor is maintained for a period of time. This phenomenon is described in particular in FR1559155.

On the other hand, the effect of a temperature change of the heavy fuel oil is not instantaneous, principally due to the inertia of the above-mentioned liquid fuel heating device.

Due to the intrinsic characteristics of the liquid fuel delivery circuit, the temperature of the heavy fuel oil is constrained in practice by a permissible minimum value and maximum value. The latter frame a nominal operating temperature determined according to the physicochemical characteristics of the fuel.

The minimum temperature of the heavy fuel oil generally corresponds to the maximum viscosity of the fuel. While the maximum temperature of the fuel oil is essentially determined by the characteristics of the auxiliary equipment installed in the fuel supply circuit (e.g. valves, filters, pumps).

In addition, the combustion systems typically use a fraction of compressed air extracted from the compressor of the turbine to achieve the atomization of the fuel oil in the combustion chamber(s). The fraction of the extracted air is cooled and compressed again such that the pressure ratio between the atomizing air and the compressor air is preferably between 1.1 and 1.8.

The atomization efficiency of the fuel in the combustion chamber(s) will be improved with a decrease in viscosity and an increase in the temperature of the fuel oil or with an increase in the pressure of the atomizing air.

Thus, the concentration of emission dust can depend directly or indirectly on the temperature and viscosity of the fuel oil, the pressure parameters of the atomizing air as well as the flow rate of the soot inhibitor.

However, soot inhibitors have disadvantages related to the cost of purchase, supply, storage and the means to be implemented to inject them into the fuel.

The use of electricity and/or steam for the heating of oil has the disadvantage of reducing the overall efficiency of a thermal power plant comprising a gas turbine. Thus, the emission reduction operation may depend on several parameters. Optimizing these operating parameters can improve the efficiency of the overall turbine cycle and reduce the cost associated with the use of the soot inhibitor.

BRIEF DESCRIPTION OF THE DISCLOSURE

The invention provides a method of optimizing the limitation of dust emissions for gas turbines or combustion plants fueled with heavy fuel oil, while avoiding the difficulties encountered in the prior art.

Further, the invention provides a method of optimizing the limitation of dust emissions for gas turbines fueled with heavy fuel oil particularly adapted to difficult economic conditions.

The invention further provides a method of optimizing the limitation of the dust emissions of a gas turbine or combustion plant comprising:

a liquid fuel oil supply line connecting a fuel source to at least one combustion chamber, comprising means for controlling the temperature of the fuel oil, and means for storing and controlling the injection of a soot inhibitor, a line for generating fuel oil atomizing air, connecting a main compressor to at least one combustion chamber, comprising means for controlling the temperature, flow rate and pressure of the fuel oil atomizing air, a central controller receiving information on the fuel oil temperature, fuel oil viscosity, pressure of the fuel oil atomizing air, and combustion gas exhaust dust concentration, and controlling a device for controlling the temperature of the fuel oil, a valve for controlling the atomizing air flow of the fuel oil, and a device for controlling the injection of a soot inhibitor, the method being characterized in that it comprises:

a first step, from a nominal temperature of the fuel oil and a nominal pressure ratio of the atomizing air of the fuel oil, and by controlling the injection of a soot inhibitor, of defining a nominal operating point corresponding to the maximum permissible level of emitted dust;

a second step of controlling a first parameter, taken from the group of the fuel oil temperature and the ratio of the pressure of the fuel oil atomizing air, in order to reach another operating point; and a third step of controlling the injection of a soot inhibitor to reach the maximum permissible level of emitted dust.

According to one embodiment of the invention, the three steps take place under the control of the central controller.

According to one embodiment of the invention, after the third step, the central controller triggers a new, second control step of the second parameter taken from the group of the fuel oil temperature and the atomizing air pressure ratio of the fuel oil.

According to one embodiment of the invention, the control of the first parameter is controlled between a minimum value and a maximum value.

According to one embodiment of the invention, the control of the temperature of the fuel oil is controlled between 50° C. and 135° C.

According to one embodiment of the invention, the pressure ratio of the fuel oil atomizing air is controlled between 1.1 and 1.8.

The method thus takes into account the cost associated with the energy consumption required to control the fuel oil temperature, the atomizing air pressure ratio, and the soot inhibitor consumption.

The method uses devices permitting the continuous measurement of the:

viscosity of the heavy fuel oil
temperature of the heavy fuel oil
mass flow in the soot inhibitors
air flow entering the compressor.
pressure ratio
concentration of solid particles emitted by the combustion.

The invention also relates to a gas turbine or combustion plant comprising:

a liquid fuel oil supply line connecting a fuel source to at least one combustion chamber, comprising means for controlling the temperature of the fuel oil, and means for storing and controlling the injection of a soot inhibitor, a line for generating fuel oil atomizing air, connecting a main compressor to at least one combustion chamber, comprising means for controlling the temperature, flow rate and pressure of the fuel oil atomizing air, a central controller receiving information from the means of measuring the fuel oil temperature, fuel oil viscosity, pressure of the fuel oil atomizing air, and combustion gas exhaust dust concentration, and controlling a device for controlling the temperature of the fuel oil, a valve for controlling the atomizing air flow of the fuel oil, and a device for controlling the injection of a soot inhibitor, characterized in that the central controller limits the dust emissions by applying the above-mentioned method.

BRIEF DESCRIPTION OF THE FIGURES

Other characteristics and advantages of the invention will become apparent on reading the following description, given solely by way of nonlimiting example, with reference to the accompanying drawings, in which.

DETAILED DESCRIPTION

Figure 1:
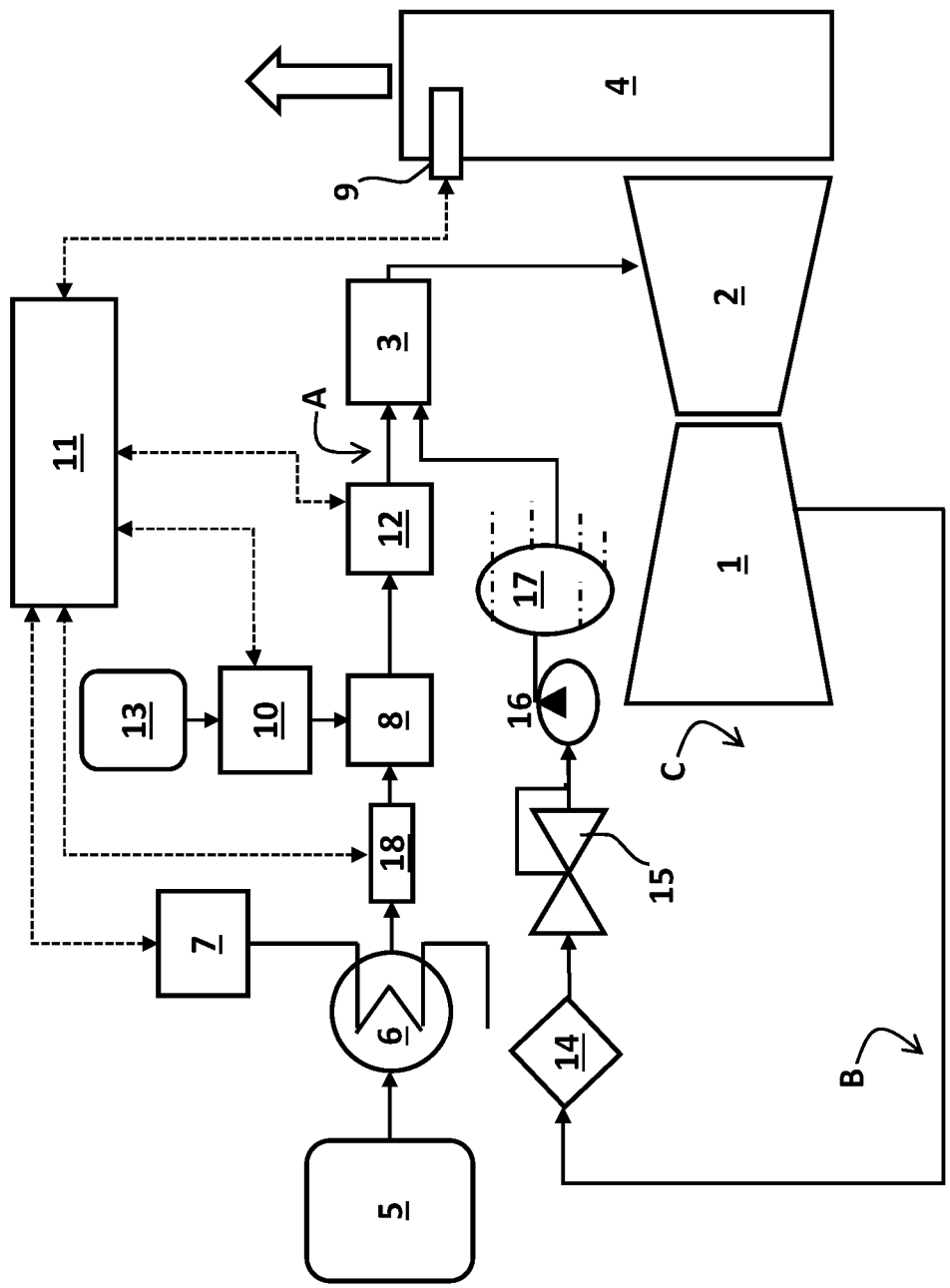
FIG. 1 is a block diagram illustrating an installation comprising a gas turbine, a controller, a fuel supply and compressed air.

FIG. 1 describes an installation including the necessary equipment for implementing the method. The gas turbine assembly is composed of a main compressor (1) connected by a shaft (C) to an expansion turbine (2), and between the two, at least one combustion chamber (3), and at the outlet a chimney (4). Of course, the shaft (C) also connects the expansion turbine (2) to either an alternator (not shown) or to a steam recovery boiler (not shown).

The turbine assembly is supplied with liquid fuel oil via the supply line A that connects a tank (5) and combustion chambers (3).

The supply line A comprises a heat exchanger (6) connected to a temperature control device (7) for adapting the temperature of the fuel oil measured by the means (18) upstream of the combustion, a device permitting the continuous measurement of the viscosity (12), a tank (13) for a soot inhibitor, an injection device (8) for injecting said inhibitor, for example a mixer, and between the two a device (10) for controlling the injection of the soot inhibitor into the fuel oil, for example a pump.

In addition, a part of the air leaving the last stages of the compressor (1) is conveyed by the line B to be used for the atomization of the fuel oil. The line B comprises an exchanger (14) for reducing the temperature of the air coming from the compressor (1), a valve (15) for controlling the atomizing air flow, and an air compressor (16) having as its energy source a motor or a reduction shaft connected to the main shaft line (C). Preferably, the atomizing air line B permits the adjustment of the pressure ratio between 1.1 and 1.8. The air thus compressed is distributed to the combustion chambers (3) by the device (17).

At the exhaust in the chimney (4), there is a device for measuring the dust concentration (9).

The controller (11) receives the signals from the online viscosity measuring device (12) and the dust concentration measuring device (9). The controller (11) is adapted to control the fuel temperature (7), the inhibitor flow control device (10), and the air flow control valve (15) placed upstream of the atomizing air compressor (16).

Figure 2:
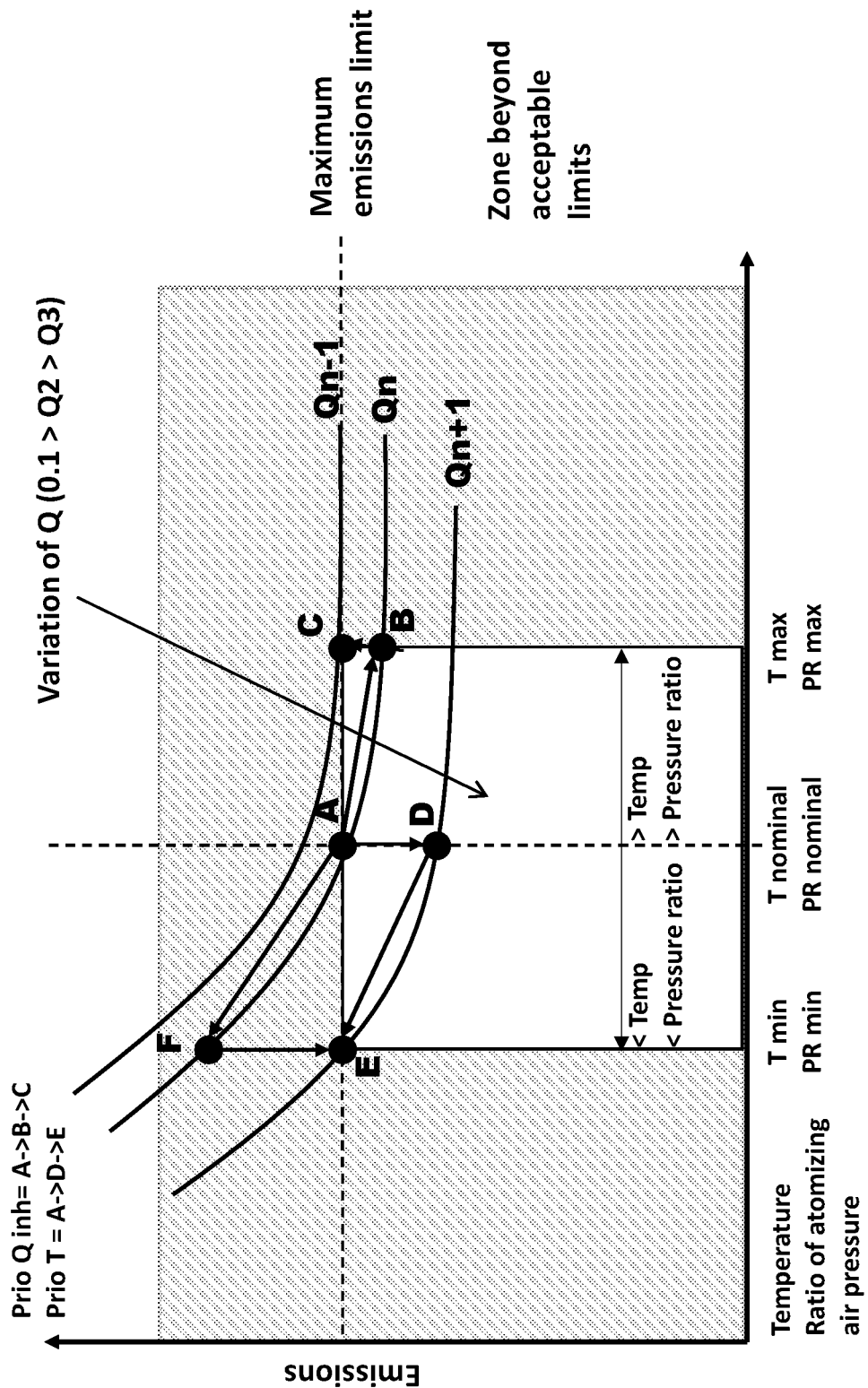
FIG. 2 shows a graph illustrating, on the X-axis, the measurement of soot emissions and on the Y-axis the temperature of the fuel oil and/or the pressure ratio, with several constant flow rate curves for the emissions inhibitor.

FIG. 2 is an illustration of the general principle of the method for optimizing the operation of reducing dust emissions. The graph in FIG. 2 represents several dust emission curves at a given inhibitor flow rate (Qn) as a function of the temperature (T) of the fuel oil and/or the pressure ratio (Pr), whereby this figure illustrates three different inhibitor flow levels Qn. The inhibitor flow rate Qn can also express the ratio between the inhibitor flow rate and the fuel oil flow rate, in order to consider the variation of the fuel oil flow rate as a function of the load of the gas turbine. It is thus possible to represent the variation in the dust emissions level as a function of the inhibitor flow rate, the fuel oil temperature and/or the pressure ratio. The graph in FIG. 2 also shows a region delimited on the X-axis by the maximum dust emissions level and delimited on the Y-axis either by the temperature T of the fuel oil or by the pressure ratio PR of the atomizing air.

In addition, for a minimum temperature, it will be necessary to reach a maximum pressure ratio, because the more the temperature of the fuel oil decreases, the more the viscosity increases, and it will be necessary to increase the pressure ratio to ensure good atomization of the fuel oil. Conversely, for a maximum temperature. It would be possible to reduce the pressure ratio, because the viscosity of the fuel oil decreases with increasing temperature.

For a constant inhibitor flow rate (Qn), the graph shows the effect on emissions of a control change in the temperature and/or the pressure ratio. Indeed, for a given inhibitor flow rate, an increase in temperature makes it possible to reduce the emissions level. Conversely, for a constant inhibitor flow rate, a decrease in temperature causes an increase in the emissions level. This is a consequence of the viscosity change. Consequently, the combustion of the fuel oil tends to increase the emissions level when the viscosity of the fuel oil increases without changing the pressure ratio.

The temperature of the fuel oil in the supply line A can be controlled between a minimum value, for example 50° C., for which the viscosity is at the maximum, and a maximum operating temperature value of the components determined during the definition of the components in the line A, for example 135° C.

Subsequently, the method according to the invention makes it possible to find an operating point on the graph for a given inhibitor flow rate for which the fuel oil temperature and/or the pressure ratio make it possible to maintain a concentration of soot in the exhaust that is lower than the maximum limit.

For each coordinate on the graph, it is possible to calculate a cost associated with the soot reduction operation. For example, this can be the cost associated with the temperature change of the fuel oil in an exchanger, the total exchanged power expressed in kW or kCal/h, the power in kW of an electrical resistance or a steam flow rate, or the power in kW consumed by the atomizing air compressor that depends on the atomizing air mass flow set by the flow rate control valve (15).

In particular, when the purchase price of electricity in €/kW is greater than a break-even point, it will then be preferable to increase the electricity production towards the electricity grid and to reduce the energy consumption necessary for heating the fuel oil and/or the pressure ratio. However, in order to reduce the dust emissions level, it is necessary to increase the inhibitor flow rate.

In addition, the consumption of the soot inhibitor generates a cost associated with its consumption and storage. In addition, in the event of a stock shortage, the cost of supply as well as the cost of the tax to be paid on dust emissions must be considered in the event that the maximum emission threshold is exceeded. In this case, the method allows the use of the inhibitor to be reduced (by reducing the flow rate) and an increase in the fuel oil temperature and/or the pressure ratio to ensure an acceptable dust emissions level.

Figure 3:
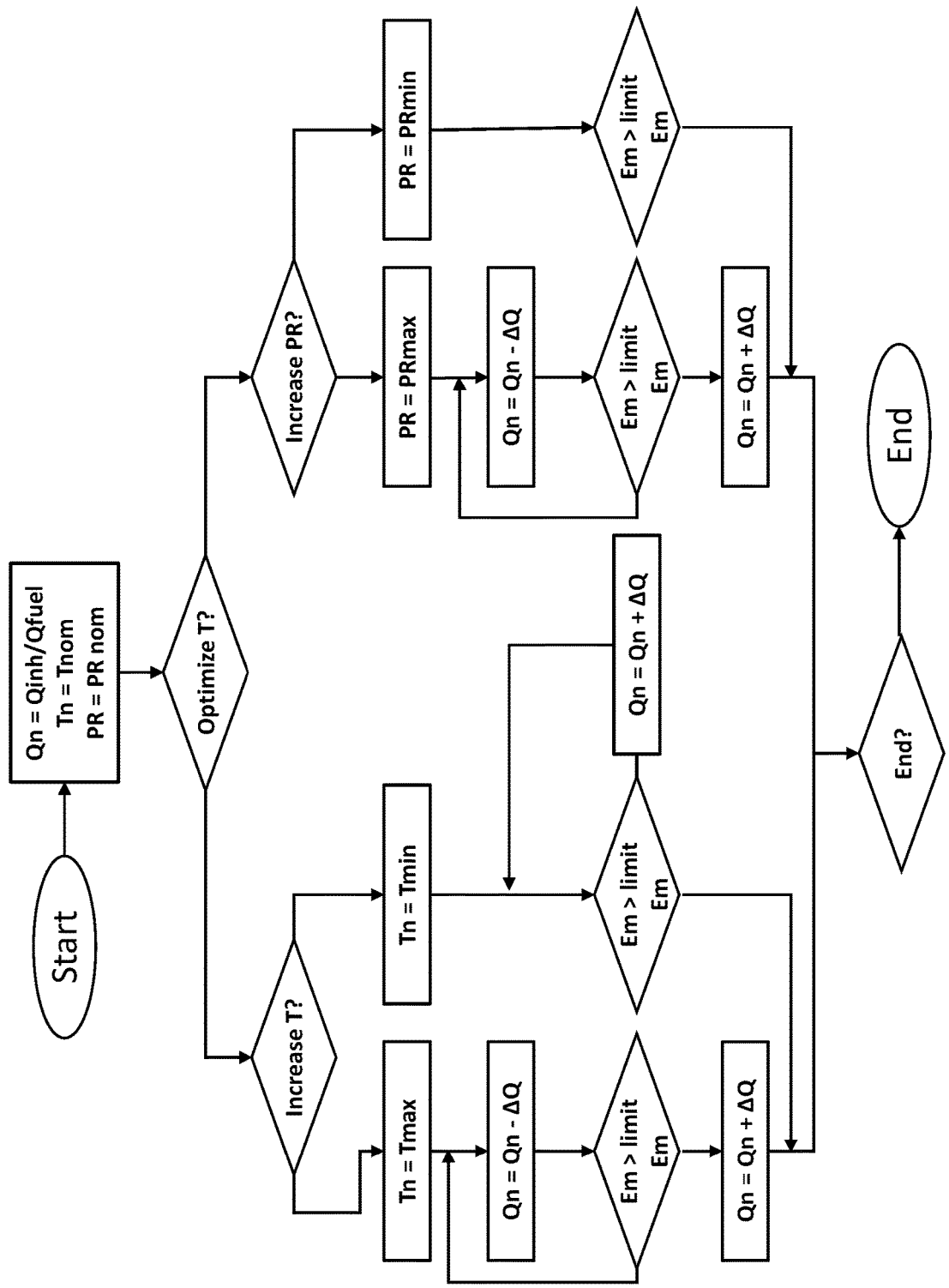
FIG. 3 shows a flow chart describing the method according to the invention.

FIG. 3 shows a flow chart detailing the method that is an embodiment of the present invention.

In a first step, for a nominal temperature and a nominal operating pressure ratio, a nominal inhibitor flow rate is calculated that is a function of the fuel oil flow rate, in order to ensure an emissions level below the maximum limit (point A, FIG. 2). The controller (11) thus provides the nominal inhibitor flow rate by sending an instruction to the injection control device (10) of the inhibitor.

In a second step, it is necessary to choose between the optimization of the fuel oil temperature and the optimization of the atomizing air pressure ratio.

According to the method, a choice must be made such that the controller (11) can adjust the fuel temperature to its minimum or maximum permissible value.

If the use of the maximum temperature is chosen, then the controller (11) sends an instruction to the temperature control device (7) to reach the maximum temperature (point B, FIG. 2). Subsequently, the controller (11) sends an instruction to the injection control device (10) of the soot inhibitor to gradually reduce the inhibitor flow rate (point C, FIG. 2). For example, the inhibitor flow rate is reduced by 10% from its initial level. The dust concentrations are measured by the device (9): if the maximum permissible limit is exceeded, the controller (11) restores the previously used inhibitor flow rate by sending an instruction to the inhibitor injection control device (10). This operation has the advantage of reducing the consumption of soot inhibitor despite the energy consumption associated with the heating of the fuel oil.

In the case where it is chosen to use the minimum temperature, then the controller (11) sends an instruction to the temperature control device (7) to reach the minimum temperature (point F, FIG. 2). Subsequently, the controller (11) sends an instruction to the inhibitor injection control device (10) to increase its flow rate until the dust concentration level measured by the means (9) is less than or equal to the maximum permissible level (point E, FIG. 2). This operation has the advantage of reducing the energy consumption of the fuel oil heating device despite the consumption of the inhibitor.

Once this step has been performed, the controller (11) returns to the second step and optimizes the atomization pressure ratio by sending an instruction to the air flow control valve (15) to change the atomizing air pressure ratio.

If the choice is made to increase the atomization pressure ratio, then the controller (11) sends an instruction to the air flow control valve (15) on line B (FIG. 1) to increase the flow rate and pressure ratio in the compressor (16) (point B, FIG. 2). Subsequently, the controller sends an instruction to the inhibitor injection control device (10) to decrease its flow rate until the dust concentration level measured by the means (9) is less than or equal to the maximum permissible level (point C, FIG. 2).

If the choice is made to use the minimum pressure ratio (point F, FIG. 2), then the controller (11) sends an instruction to the inhibitor injection control device (10) to increase its flow rate until the dust concentration level measured by the means (9) is less than or equal to the maximum permissible level (point E, FIG. 2).

From the nominal operating point (point A, FIG. 2), to be able to reach the point E corresponding to the minimum fuel oil temperature, or the minimum pressure ratio, and the maximum dust emission limit, it is possible to start with an increase in the injection of the soot inhibitor (point D, FIG. 2) and then command the decrease in the fuel oil temperature or the pressure ratio to reach the point E.

It is expected that it is possible to perform a change in the fuel oil temperature and then the pressure ratio, or conversely a change in the pressure ratio and then a change in the temperature of the fuel oil.

The present invention thus makes it possible to optimize the operation for reducing the soot emissions of a gas turbine or combustion plant supplied with fuel oil from a technical and economic point of view, either by reducing the energy provided to maintain the temperature of the fuel oil and/or a pressure ratio of the atomizing air, or by reducing the injection rate of the soot inhibitor.

In summary, the minimum fuel oil temperature and/or the maximum pressure ratio will preferably be chosen when the price of the electricity produced is greater than a break-even point, for example during the day and/or when the volume of the inhibitor in stock is greater than a predefined level.

The maximum fuel oil temperature and/or the minimum pressure ratio will preferably be chosen when the price of the electricity produced is greater than a break-even point, for example during the night and/or when the volume of the inhibitor in stock is lower than a predefined level.

What we claim is:

1. A method for optimizing a limitation of dust emissions of a gas turbine comprising:
    a liquid fuel oil supply line connecting a fuel source to at least one combustion chamber, the liquid fuel oil supply line comprising a heat exchanger for controlling a temperature of liquid fuel oil supplied from the fuel source, a tank for storing a soot inhibitor, and a mixer and a pump for and controlling an injection of the soot inhibitor;
    a line for generating fuel oil atomizing air, the line connecting a main compressor to the at least one combustion chamber, the line comprising an exchanger for controlling a temperature of the fuel oil atomizing air, a valve for controlling a flow rate of the fuel oil atomizing air, and wherein the main compressor controls an air pressure of the fuel oil atomizing air; and
    a central controller receiving information on the temperature of the liquid fuel oil, a viscosity of the liquid fuel oil, the air pressure of the fuel oil atomizing air, and a combustion gas exhaust dust concentration, and controlling the temperature of the liquid fuel oil and the injection of the soot inhibitor;
    the method comprising:
    a first step, from a nominal temperature of the liquid fuel oil and a nominal pressure ratio of the fuel oil atomizing air, and by controlling the injection of the soot inhibitor, defining a nominal operating point corresponding to the maximum permissible level of emitted dust;
    a second step of controlling a first parameter, taken from a group of the temperature of the liquid fuel oil and the pressure ratio of the fuel oil atomizing air, in order to reach another operating point; and
    a third step of controlling the injection of the soot inhibitor to reach the maximum permissible level of emitted dust.

2. The method according to claim 1, wherein the first step, the second step, and the third step take place under the control of the central controller.

3. The method according to claim 2, wherein after the third step, the central controller triggers a fourth control step of controlling a second parameter taken from the group of the temperature of the liquid fuel oil and the pressure ratio of the fuel oil atomizing air.

4. The method according to claim 1, wherein the control of the first parameter is controlled between a minimum value and a maximum value.

5. The method according to claim 4, wherein the control of the temperature of the liquid fuel oil is controlled between 50° C. and 135° C.

6. The method according to claim 4, wherein the pressure ratio of the fuel oil atomizing air is controlled between 1.1 and 1.8.

7. A gas turbine or combustion plant comprising:
    a liquid fuel oil supply line connecting a fuel source to at least one combustion chamber, the liquid fuel oil supply line comprising a heat exchanger for controlling a temperature of liquid fuel oil supplied from the fuel source, a tank for storing a soot inhibitor, and a mixer and a pump for and controlling an injection of the soot inhibitor;
    a line for generating fuel oil atomizing air, the line connecting a main compressor to the at least one combustion chamber, the line comprising an exchanger for controlling a temperature of the fuel oil atomizing air, a valve for controlling a flow rate of the fuel oil atomizing air, and wherein the main compressor controls an air pressure of the fuel oil atomizing air;
    a central controller receiving information on the temperature of the liquid fuel oil, viscosity of the liquid fuel oil, the air pressure of the fuel oil atomizing air, and combustion gas exhaust dust concentration; and controlling the temperature of the liquid fuel oil and the injection of the soot inhibitor, wherein the central controller limits the dust emissions by applying the method according to claim 1.

8. A method for optimizing a limitation of dust emissions of a combustion plant comprising:
    a gas turbine having a main compressor and at least one combustion chamber downstream from the main compressor;
    a liquid fuel oil supply line connecting a fuel source to the at least one combustion chamber, wherein the liquid fuel oil supply line comprises a heat exchanger for controlling a temperature of liquid fuel oil supplied from the fuel source, a tank for storing a soot inhibitor, and a mixer and a pump for and controlling an injection of the soot inhibitor;
    a line for generating fuel oil atomizing air, the line connecting the main compressor to the at least one combustion chamber, the line comprising an exchanger for controlling a temperature of the fuel oil atomizing air, a valve for controlling a flow rate of the fuel oil atomizing air, and wherein the main compressor controls an air pressure of the fuel oil atomizing air;

a central controller receiving information on the temperature of the liquid fuel oil, a viscosity of the liquid fuel oil, the air pressure of the fuel oil atomizing air, and a combustion gas exhaust dust concentration, and controlling the temperature of the liquid fuel oil and the injection of the soot inhibitor;

the method comprising:
- as a first step, defining a nominal operating point corresponding to the maximum permissible level of emitted dust, based on a nominal temperature of the liquid fuel oil, a nominal pressure ratio of the fuel oil atomizing air, and control of the injection of the soot inhibitor;
- as a second step, controlling a first parameter, selected from a group of the temperature of the liquid fuel oil and the pressure ratio of the fuel oil atomizing air, in order to reach another operating point; and
- as a third step, controlling the injection of the soot inhibitor to reach the maximum permissible level of emitted dust.

9. The method according to claim 8, wherein the first step, the second step, and the third step take place under the control of the central controller.

10. The method according to claim 9, wherein after the third step, the central controller triggers a fourth control step of controlling a second parameter taken from the group of the temperature of the liquid fuel oil and the pressure ratio of the fuel oil atomizing air.

11. The method according to claim 8, wherein the control of the first parameter is controlled between a minimum value and a maximum value.

12. The method according to claim 11, wherein the control of the temperature of the liquid fuel oil is controlled between 50° C. and 135° C.

13. The method according to claim 11, wherein the pressure ratio of the fuel oil atomizing air is controlled between 1.1 and 1.8.

* * * * *

UNITED STATES PATENT AND TRADEMARK OFFICE
CERTIFICATE OF CORRECTION

PATENT NO. : 11,230,977 B2  
APPLICATION NO. : 16/227384  
DATED : January 25, 2022  
INVENTOR(S) : Matthieu Vierling et al.

Page 1 of 1

It is certified that error appears in the above-identified patent and that said Letters Patent is hereby corrected as shown below:

On the Title Page

Item (73) Assignee should read:  
GE Energy Products France SNC  
Parc Activités Techn'hom  
24 Avenue Du Maréchal Juin Bp 40437  
Belfort 90000  
France Signed and Sealed this  
Seventh Day of February, 2023

Katherine Kelly Vidal  
*Director of the United States Patent and Trademark Office*